US005591479A

United States Patent [19]
Ponroy

[11] Patent Number: 5,591,479
[45] Date of Patent: Jan. 7, 1997

[54] BRAIN PHOSPHOLIPID COMPOSITION AND METHOD OF MAKING FOR AN INFANT FORMULA

[75] Inventor: Yves Ponroy, Versailles, France

[73] Assignee: Institut de Recherche Biologique, France

[21] Appl. No.: 496,326

[22] Filed: Jun. 29, 1995

[51] Int. Cl.[6] ..................................................... A23J 7/00
[52] U.S. Cl. ........................... 426/662; 426/74; 426/429; 426/437; 426/604; 426/613
[58] Field of Search ............................. 426/74, 604, 613, 426/662, 429, 437

[56]  References Cited

U.S. PATENT DOCUMENTS

| 2,358,869 | 9/1924 | Maurer et al. | 426/429 |
| 4,166,823 | 9/1979 | Sietz | 426/662 |
| 4,234,619 | 11/1980 | Yano et al. | 426/429 |
| 5,336,792 | 8/1994 | Sola et al. | 426/429 |

FOREIGN PATENT DOCUMENTS

| 1326326 | 4/1963 | France . | |
| 1957M | 8/1963 | France . | |
| 62-29951 | 2/1987 | Japan . | |
| 62-262998 | 11/1987 | Japan | 426/662 |
| 9222291 | 12/1992 | WIPO . | |

OTHER PUBLICATIONS

Patent Abstracts of Japan, vol. 11, No. 206 (C–433), Jul. 3, 1987.

*Primary Examiner*—Helen Pratt
*Attorney, Agent, or Firm*— Gifford, Krass, Groh, Sprinkle, Patmore, Anderson & Citkowski, P.C.

[57]  ABSTRACT

The present invention relates to the domain of food and more particularly to the domain of nutritional supplements for the food of delicate or malnutritioned patients to food compositions, intended for premature or low-weight babies, which contain as a physiological source of polyunsaturated fatty acids of the n–3 series, mammalian brain phospholipids, in combination with or mixed with a food support for the food of very young children and a process for obtaining mammalian brain phospholipids.

12 Claims, No Drawings

BRAIN PHOSPHOLIPID COMPOSITION AND METHOD OF MAKING FOR AN INFANT FORMULA

The present invention relates to the domain of food and in particular to the domain of the supplementation of food with necessary or useful elements.

A more particular subject of the invention is new food compositions intended to compensate for essential fatty acid deficiencies in the food of delicate or malnutritioned patients.

It is known in particular that the specific needs of pregnant women with regard to essential fatty acids and particularly alpha-linolenic acid (18:3 n–3) are often not sufficiently provided for because the diet and mainly the usual fatty substances are lacking in such acids and the daily supply is low if not to say insufficient. This can result in harmful implications in the cerebral development of fetuses, or in new-born babies, more particularly in premature babies. Recent articles, which have appeared in the literature (cf. Crawford Ann. J. Clin. Nutr. (1993) 57(suppl)—p. 703–710), have underlined the importance of the role played by these polyunsaturated fatty acids of a particular type, for the development of the nerve cells and the formation of the walls of their membranes.

Added to this is the fact that premature babies and low birth-weight babies have a greater need for polyunsaturated fatty acids than other infants, which is not satisfied either by the present artificial milks, which do not contain many of these acids, or by the mother's milk given that lactating mothers are often deficient in such fatty acids.

Moreover, when artificial milks contain a sufficient quantity of linoleic acid ($C_{18}$:2 n–6) and alpha-linolenic acid ($C_{18}$:3 n–3) the enzymatic provision of premature babies with useful enzymes (Δ6-desaturases) is too low to convert them into higher homologues and, in particular, into docosahexenoic acid ($C_{22}$:6 n–3), and into arachidonic acid ($C_{20}$–4 n–6). A recent article by M. FIREMAN (Ann. J. Clin. Nutr. (1993) 57(suppl.)—p. 829) reviews this problem of enzymatic provision.

The problem of the present invention is therefore to produce a supply of a necessary and sufficient quantity of these two fatty acids which seem to be essential for ensuring the correct development of vision (P. PEIRANO J. P ediatr. 120 (1992) 168°180) in premature babies as well as for ensuring a satisfactory regulation of the growth of other cerebral functions in premature babies which cannot be breast-fed.

Studies carried out by American scientists (D. R. HOFFMANN Ann. J. Clin. Nutr. (1993) 57(suppl.) p. 807–812), have shown that the functions of light reception in premature babies undergo an optimal development when a sufficient and assimilable supply of polyunsaturated long-chain fatty acids, belonging to the n–3 series, is provided, either by the addition to mother's milk, or by incorporation in the diet of fish oils.

It has even been possible to reveal (K. BJERVE Ann. J. Clin. Nutr. (1993) 57(suppl.) p. 801–806S) a correlation between the levels of docosahexenoic acid (DHA) in the plasma of new-born babies and their degree of prematurity, evaluated according to the indices of psychomotor and mental development.

The problem therefore consisted of finding suitable sources of docosahexenoic acid. Fish oil was the first choice but this has the disadvantage of containing a high percentage of eicosapentenoic acid (EPA $C_{20}$–5 n–3) whose presence can be dangerous in babies and which is not normally found in mother's milk (cf. K. BJERVE).

Consequently the invention resides in the fact that a physiological source of polyunsaturated fatty acids of the n–3 series and in particular of DHA can be supplied, in physiological proportion, which can be used as it is or which can be incorporated in the composition of an infant milk or of a food supplement for premature babies or low birth-weight babies.

Therefore a subject of the invention is food compositions which can be directly incorporated in the food of very young children characterized in that they contain, as a food supply, mammalian brain phospholipids combined or mixed with a food support suitable for the food of very young children.

In particular, the mammalian brain phospholipids are pig brain phospholipids. They have the following chemical structure:

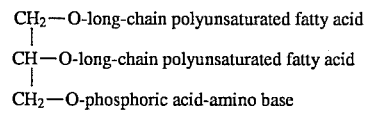

The amino base is, according to the phospholipids: choline, serine, ethanolamine or inositol.

The brain of mammals and quite particularly that of pigs contains a fairly constant proportion of the following phospholipids:

| | |
|---|---|
| sphingomyelin | 4–7% |
| phosphatidylcholine | 20–30% |
| phosphatidylserine | |
| phosphatidylinositol | 17–25% |
| phosphatidylethanolamine | 30–40% |

These cerebral phospholipids have a specificity which clearly distinguishes them from the other sources of phospholipids, animal or vegetable, such as animal lecithins or soya lecithins. This specificity is due in particular to the chemical nature of the fatty acids of which they are composed.

Analysis of the fatty acids which esterify the glycerol molecule shows that they are divided up as follows, on average:

| | | |
|---|---|---|
| Oleic acid | 18:1 n-9 | about 25% |
| Linoleic acid | 18:2 n-6 | less than 1% |
| γ-linolenic acid | 18:3 n-6 | less than 0.5% |
| Arachidonic acid | 20:4 n-6 | about 8.5% |
| Acid in | 22:4 n-6 | about 4% |
| Acid in | 22:5 n-6 | about 0.8% |
| Alpha-linolenic acid | 18:3 n-3 | |
| Stearidonic acid | 18:4 n-3 | |
| EPA (eicosapentenoic acid) | 20:5 n-3 | less than 1% |
| Acid in | 22:5 n-3 | less than 1% |
| DHA (docosahexenoic acid) | 22:6 n-3 | about 9% |

The experiments carried out indicated that the fatty acids contained in the cerebral phospholipids of mammals have the advantage, with regard to the supplementation of premature babies:

of containing about 10% of DHA (22:6 n–3) and only 0.3% of EPA (20:5 n–3)

of the fact that the ratio of polyunsaturated long-chain fatty acids, relative to those with a shorter chain (PUFA-LC) is satisfactory:

$$\frac{\text{PUFA-LC n-6}}{\text{PUFA-LC n-3}} = 1.5$$

In FRANCE, this ratio is about 2 in mother's milk (cf. G. DURAND Europ. J. Clin. Nutr. (1993) 47(suppl.) p. 700–710).

- that the cerebral phospholipids contain 8 to 9% of arachidonic acid (20:4 n–3) which, like DHA, seems to be essential for the brain of premature babies.
- that the cerebral phospholipids contain almost 25% of polyunsaturated fatty acids higher than C18.

The cerebral phospholipids according to the invention are therefore capable of supplying premature babies with physiological and balanced doses of the various fatty acids which they need for their cerebral development. Recent studies prove that a supply of cerebral phospholipids, according to the invention, cause a more efficient increase in DHA (22:6 n–3) at the level of the cerebral structures and the retina than a supply of triglycerides rich in alpha-linolenic acid (18:3 n–3).

The invention also relates to a process for obtaining cerebral phospholipids and in particular those of pigs, which consists of removing, by mechanical means, the brains from freshly-slaughtered animals, freezing them immediately at −20° C. and storing them at this temperature, then allowing the temperature of the organs to rise to a temperature comprised between −5° and 0° C. before mincing them in an industrial mincing machine then in grinding machines, so as to obtain a fluid paste the water content of which is about 80%, eliminating the water from the tissues by transferring the fluid paste thus obtained to the top of an atomization chamber and rapidly evaporating the water in a current of air superheated to 190°–195° C., separating the lipid fraction from the resultant powder by introducing it into a mixture of $C_6$ aliphatic hydrocarbons and maintaining it under agitation at ambient temperature, then filtering the mixture obtained and concentrating the liquid phase separated off under reduced pressure, in order to obtain a crude paste which is poured into acetone which has had a food antioxidizing agent added to it beforehand, the precipitate formed being separated off by filtration under a nitrogen atmosphere and the pulverulent product thus collected being dried under vacuum.

The phospholipid powder can then be diluted or incorporated in inert supports or vehicles suitable for the food of very young children. Thus the cerebral phospholipids could be diluted with a digestible support such as lactose, casein, milk powder or predigested flours. According to the case, the support is capable of supplying calories in small quantities or in larger quantities.

The phospholipids according to the invention can also be formulated in liquid form and in particular in suspension in an aqueous vehicle such as table water, sugar water or equivalent vehicles.

The cerebral phospholipids according to the invention can also be formulated in the form of emulsions and in particular liposomes. The liposomes can be constituted by particles whose size varies or is mainly within a range of 100 to 500 μm. They can remain in liquid phase or be dehydrated in order to be mixed with a solid food diluting agent.

The food supplements thus produced can, in addition, have other growth factors added to them such as vitamins (vitamins A, D or B group vitamins), mineral elements, biological factors, essential amino acids.

As mineral elements there can be mentioned in particular salts of calcium, magnesium, zinc or iron which play a role in the well-being of very young children.

As biological growth factors there can be mentioned in particular taurine, choline, calcium inositol hexaphosphate.

As an essential amino acid there can be mentioned arginine or lysine.

The food supplements according to the invention can contain from 1 to 20% of cerebral phospholipids and are used by dilution in feeding bottles if the mixture is totally soluble or in the form of drops of aqueous suspension or of emulsion. This latter form of use is preferred and allows a more accurate determination of the quantity of cerebral phospholipids according to the invention, added as a supplement to the food of very young children.

The following examples illustrate the invention. They do not limit it in any way.

EXAMPLE I

| | |
|---|---|
| Powdered pig cerebral phospholipids | 25 g |
| Milk casein | 20 g |
| Brewer's yeast extract | 0.5 g |
| Wheat starch | 12 g |
| Alpha-tocopherol | 0.2 g |
| Calcium carbonate | 2.3 g | for 100 sachets of powder containing 0.25 g of phospholipids to be incorporated in the feeding bottle or to be diluted in a small amount of sugar water.

EXAMPLE II

| | |
|---|---|
| Powdered pig cerebral phospholipids | 40 g |
| Hydroxy ethyl cellulose | 2 g |
| Ethylene oxide/propylene oxide copolymer marketed under the trademark Pluronic F18 | 8 g |
| Vitamin B12 | 5 mg |
| Calcium gluconate | 0.500 g |
| Ferrous gluconate | 0.250 g |
| Ascorbyl palmitate | 0.100 g |
| Sodium alginate | 4 g |
| Water sqf | 100 ml | the emulsion thus produced is intended to be incorporated in the milk for new-born babies.

EXAMPLE III

| | |
|---|---|
| Powdered pig cerebral phospholipids | 25 g |
| Skimmed milk powder | 25 g |
| Tricalcium phosphate | 2 g |
| Ferrous carbonate | 1 g |
| Manganese carbonate | 1 g |
| Vitamin B complex | 0.2 g |
| Microcrystalline cellulose | 26 g |

The powder thus obtained can be divided into 0.100 g sachets in the milk for new-born babies.

EXAMPLE IV

| | |
|---|---|
| Powdered pig cerebral phospholipids | 45 g |
| Hydroxy ethyl cellulose | 2 g |
| Ethylene oxide/propylene oxide copolymer marketed under the trademark Pluronic F18 | 8 g |
| Vitamin E | 0.3 g |
| Sodium alginate | 4 g |
| Water sqf | 100 ml |

The emulsion thus produced is intended to be incorporated in the milk for new-born babies.

I claim:

1. Food compositions which can be directly incorporated in the food of very young children useful as an infant formula, said food compositions comprising non-denatured mammalian brain phospholipids, said phospholipids having at least two fatty acids in the chain, in combination with or mixed with a food support suitable for such a food.

2. Food compositions according to claim 1 wherein the food carrier is a low-calorie or higher-calorie digestible substance.

3. Food compositions according to claim 1 wherein the food carrier is selected from the group consisting of lactose, casein, powdered milk, and predigested flours.

4. Food compositions according to claim 1 wherein the food support is a sweetened or non-sweetened aqueous vehicle.

5. Food compositions according to claim 1 wherein the cerebral phospholipids are formulated in the form of emulsions.

6. Food compositions according to claim 1 wherein the cerebral phospholipids are formulated in the form of liposomes whose size ranges from 100 to 500 μm.

7. Food compositions according to claim 1 wherein other growth factors are added to them.

8. Food compositions according to claim 7 wherein the growth factor is a vitamin or a mixture of vitamins.

9. Food compositions according to claim 7 wherein the growth factor is a mineral element selected from the group consisting of calcium salts, magnesium salts, zinc salts and iron salts.

10. Food compositions according to claim 1 in which the amount of cerebral phospholipids ranges from 1 to 20%.

11. A process for making the mammalian brain phospholipid composition of claim 1 which consists of removing, by mechanical means, the brains from freshly-slaughtered animals, freezing them immediately at −20° C. and storing them at this temperature, then allowing the temperature of the brains to rise to between −5° and 0° C., before mincing them in an industrial mincing machine then in grinding machines, so as to form a fluid paste, a water content of which is about 80% eliminating the water from the fluid paste by transferring the fluid paste thus obtained to the top of an atomization chamber and rapidly evaporating the water in a current of air superheated to 190°–195° C. to form a powder having a lipid fraction, separating the lipid fraction from the resultant powder by extraction with a combination of $C_6$ aliphatic hydrocarbons by stirring at ambient temperature to form a mixture having a liquid phase, filtering the mixture obtained and concentrating to dryness the liquid phase separated off under reduced pressure, in order to obtain a crude paste which is poured into acetone to form a precipitate, separating the precipitate formed by filtration under a nitrogen atmosphere and drying under vacuum to collect a pulverulent product.

12. A method for compensating the deficiencies in essential unsaturated fatty acids in the food of babies which consists in administering to premature malnutritioned babies in need thereof a safe and effective amount of cerebral phospholipids obtained according to the process of claim 11 in conjunction or admixture with a food support.

* * * * *